United States Patent [19]

Coker, Jr. et al.

[11] 4,255,096
[45] Mar. 10, 1981

[54] DRIVE FOR SYRINGE PUMP

[75] Inventors: George M. Coker, Jr., Silver Spring, Md.; Rodolfo R. Rodriquez, Buffalo Grove, Ill.

[73] Assignee: Baxter Travenol Laboratories, Inc., Deerfield, Ill.

[21] Appl. No.: 1,679

[22] Filed: Jan. 8, 1979

[51] Int. Cl.³ .................. F04B 17/00; A61M 5/20
[52] U.S. Cl. .................. 417/415; 128/218 A; 128/236; 128/DIG. 1
[58] Field of Search .................. 417/415; 128/218 A, 128/236, DIG. 1

[56] References Cited

U.S. PATENT DOCUMENTS

| | | | |
|---|---|---|---|
| 2,508,253 | 5/1950 | Haggardt | 417/415 X |
| 2,786,468 | 3/1957 | Singer et al. | 128/218 |
| 3,266,299 | 8/1966 | Swank | 417/415 X |
| 3,612,729 | 10/1971 | Commarmot | 417/415 |

Primary Examiner—Richard E. Gluck
Attorney, Agent, or Firm—R. A. Benziger; George H. Gerstman; Thomas Vigil

[57] ABSTRACT

An improved drive is provided for a syringe having a barrel and a plunger. The drive utilizes an electric motor which has an axial shaft that moves back and forth axially when the shaft is prevented from rotating. A syringe barrel holder is fixed relative to the electric motor housing and a plunger holder is rigidly fixed to the shaft. When the electric motor is energized, the plunger holder will move back and forth relative to the syringe barrel holder. A plurality of switches for controlling the electric motor are positioned in fixed locations relative to the motor housing. The plunger holder is operative to actuate and deactuate the switches during axial travel of the shaft.

11 Claims, 3 Drawing Figures

DRIVE FOR SYRINGE PUMP

BACKGROUND OF THE INVENTION

This invention concerns a novel syringe pump and, more particularly, a syringe pump utilizing an electric motor in which the shaft traverses linearly thereby providing a push-pull motion instead of a rotational motion.

Various types of motorized devices have been utilized for providing pumping action for medical syringes. Such devices generally comprise a syringe barrel that is fixed in position and a system for moving the plunger in the barrel for extracting and/or perfusing fluids.

Prior art devices are known in which movement of the plunger relative to the shaft is controlled closely in order to meter the amount of fluid that is extracted or infused.

It is an object of the present invention to provide a syringe pump that is simple in construction and economical to manufacture.

Another object of the present invention is to provide a syringe pump that permits effective and controlled metering of the fluid that is drawn into the barrel and expelled therefrom during the pumping action.

A further object of the present invention is to provide a syringe pump which utilizes a motor which can provide significant thrust to drive the plunger and which does not require rotational movement of the motor shaft.

Other objects and advantages of the present invention will become apparent as the description proceeds.

SUMMARY OF THE INVENTION

According to the invention there is provided a drive for a syringe having at least one barrel and plunger assembly, which drive comprises: an electric motor having a housing, a rotatable armature within said housing, and an axial shaft extending therefrom and having a portion thereof which is threaded and which is received through a threaded member fixed to said armature, a first holder that is fixed relative to the electric motor housing, guide means that are fixed relative to the first holder and including a track extending parallel to said shaft for guiding a portion of said drive, a second holder rigidly fixed to said shaft and slidable along said track forming part of said guide means, said guide means preventing rotational but not axial movement of said shaft upon sliding movement of said second holder fixed to said shaft on said track, said track including two elongate members fixed relative to the electric motor housing, said members being parallel spaced from each other and said shaft, and being positioned on either side of said shaft, means for connecting one of the barrel and plunger with said first holder, means connecting the other of the barrel and the plunger to said second holder, and means for coupling the electric motor to a source of current whereby energization of the electric motor will provide non-rotational axial travel of said shaft thereby causing relative movement between the syringe plunger and the syringe barrel.

In the illustrative embodiment, the electric motor comprises a reversing motor. The coupling means comprises means for connecting the electric motor to an electric current source. A plurality of switches are positioned in fixed locations relative to the track, with the switches being operative to control electrical energization of the electric motor. The second holder is operative to actuate and deactuate the switches during axial travel of said shaft.

A more detailed explanation of the invention is provided in the following description and claims, and is illustrated in the accompanying drawings.

DETAILED DESCRIPTION OF THE ILLUSTRATIVE EMBODIMENT

Figure 1:
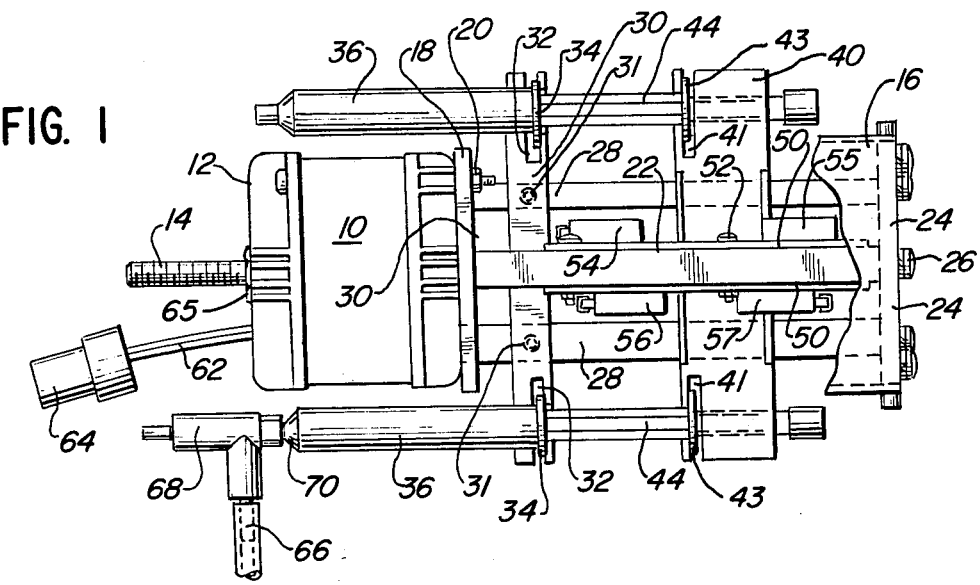
FIG. 1 is a top plan view of a syringe pump constructed in accordance with the principles of the present invention.

Referring to the drawings, the syringe pump shown therein includes an electric motor 10 (described in more detail below), with electric motor 10 having a housing 12 and a threaded shaft 14 extending axially therefrom. A syringe barrel holder assembly 16 is fastened to motor housing 12. The syringe barrel holder 16 includes a motor mounting plate 18 that is bolted to the motor housing by means of bolt-nut assemblies 20, spacer members 22 and mounting plate 24, which is positioned parallel to motor mounting plate 18 and is coupled thereto by means of screws 26 which extend through spacers 22.

A pair of guide members 28 are connected between mounting plates 18 and 24 and extend parallel to the shaft of electric motor 10. The syringe barrel holder includes a clamp member 30 that is fastened by screws 31 to tracks 28 so that the barrel clamp member 30 is fixed relative to tracks 28 and electric motor 10. Clamp member 30 defines slots 32 for receiving the flanges 34 of syringe barrels 36.

A plunger holder and clamp assembly 40 is fastened to shaft 14 of electric motor 10, by means of a screw 42. Assembly 40 defines slots 41 for receiving the flanges 42 of syringe plungers 44.

A pair of switch mounting plates 50 are fastened to spacer 22 by means of screws 52. Mounting plates 50 carry switches 54, 55, 56 and 57 which are positioned for actuation and deactuation during travel of plunger holder assembly 40, as most clearly seen in FIG. 2.

A mounting bracket 60 is connected to the barrel holder assembly for mounting the syringe pump on a suitable horizontal plane. A pair of electrical leads 62 are provided for coupling the motor 10, by means of a terminal connector 64, to a suitable electric current source. Electric motor 10 is a reversible, permanent magnet motor sold by Hurst Mfg. Corp., Princeton, Ind. 47670, Model LA Synchronous (300 rpm rotor speed). As stated above, shaft 14 of motor 10 traverses linearly thereby providing a push-pull motion instead of rotational motion. The motor includes a nut 65 captured inside the armature and located axially. Threaded shaft 14 is located within and through the nut 65 in threaded engagement therewith. When shaft 14 is free to rotate with the armature, the nut 65 and shaft 14 will turn together. However, when shaft 14 is prevented from rotating, such as by being held against rotation by means of plunger holder and clamp assembly 40 slidably engaging the two guide members 28 (FIG. 1), there will be relative motion between the nut 65 which is turning with the armature and the fixed shaft 14 which is being prevented from rotating. Therefore, shaft 14 cannot rotate but can only move axially through the nut 65.

Figure 2:
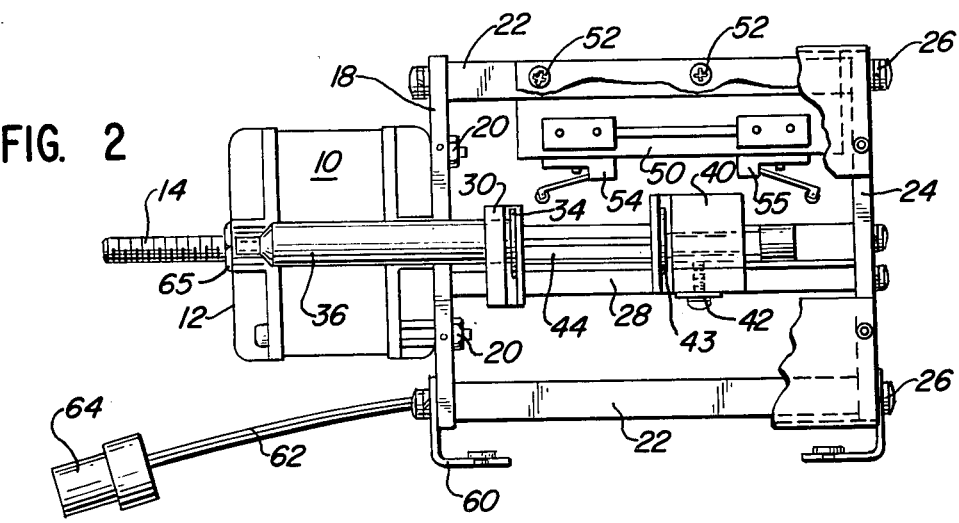
FIG. 2 is a front elevational view thereof.
Figure 3:
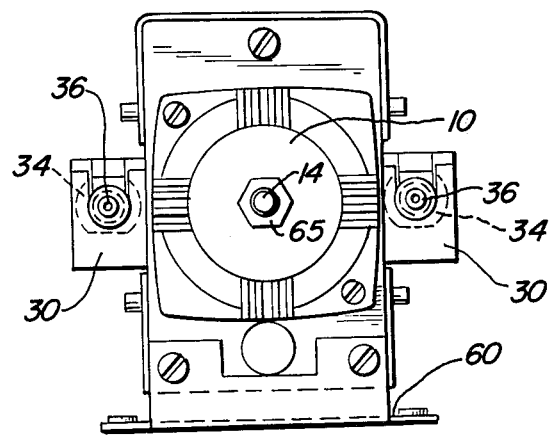
FIG. 3 is a side elevational view thereof, taken from the left side of FIG. 2.

Thus referring to FIGS. 1 and 2, it can be seen that plunger holder and clamp assembly 40 is fixed to shaft 14 and is slidable along guide members or track 28. So long as assembly 40 is fixed to shaft 14, shaft 14 cannot rotate and, when motor 10 is energized, shaft 14 is forced to move linearly. Switches 54, 55, 56 and 57 are positioned so that actuation and deactuation of these switches in a predetermined sequence will cause the motor 10 to be energized to move shaft 14 (with respect to FIGS. 1 and 2) in the rightward direction, or in the leftward direction, or to start and stop such movement as is required, switches 54 and 56 controlling the stopping and reversing of the leftward movement when engaged by plunger holder assembly 40 and switches 55 and 57 controlling the stopping and reversing of the rightward movement when engaged by plunger holder assembly 40.

In the illustrative embodiment, the syringe illustrated in the upper portion of FIG. 1 may be an air syringe while the syringe illustrated in the lower portion of FIG. 1 may be used for injecting and expelling water. To this end, a water tube assembly 66 and a check valve 68 are provided at the discharge end 70 of the syringe barrel 36.

It can be seen that a relatively simple and highly effective syringe pump has been provided which enables axial movement of the syringe plungers with respect to the syringe barrels and permits precise metering by positioning switches 54-57 in determined locations. Although an illustrative embodiment of the invention has been shown and described, it is to be understood that various modifications and substitutions may be made by those skilled in the art without departing from the novel spirit and scope of the present invention.

What is claimed is:

1. A drive for a syringe having at least one barrel and plunger assembly, which drive comprises: an electric motor having a housing, a rotatable armature within said housing and an axial shaft extending therefrom and having a portion thereof which is threaded and which is received through a threaded member fixed to said armature; a first holder that is fixed relative to the electric motor housing; guide means that is fixed relative to said first holder and including a track extending parallel to said shaft for guiding a portion of said drive; a second holder rigidly fixed to said shaft and slidable along said track; said guide means preventing rotational but not axial movement of said shaft upon sliding movement of said second holder fixed to said shaft on said track; said track including two elongate members fixed relative to the electric motor housing, said members being parallel spaced from each other and said shaft, and being positioned on either side of said shaft; means for connecting one of the barrel and the plunger with said first holder; means for connecting the other of the barrel and the plunger to said second holder; and means for coupling the electric motor to a source of current whereby energization of the electric motor will provide non-rotational axial travel of said shaft thereby causing relative movement between the syringe plunger and the syringe barrel.

2. A syringe drive as described in claim 1 including fixed means engagable by said second holder for controlling the energization of said electric motor thereby to limit axial movement of said shaft.

3. A syringe drive as described in claim 1, wherein said electric motor is a reversing motor; said coupling means comprising means for connecting said electric motor to an electric current source; and at least two switches positioned in fixed locations relative to said track at each end of the desired forward and reverse limits of movement of said second holder, said switches being operative to control electrical energization of said electric motor when engaged by said second holder at the end of the desired axial travel of said shaft in the forward or reverse direction.

4. A syringe drive as described in claim 1, wherein said electric motor includes an armature, a nut captured inside the armature and axially positioned, said shaft being threaded and located within and through said nut in threaded engagement therewith, whereby when the threaded shaft is prevented from rotating there will be relative motion between the nut which turns with the armature during energization of the electric motor and the threaded shaft thereby to move the threaded shaft axially.

5. A drive for a syringe having at least one barrel and plunger assembly, which drive comprises: an electric motor having a housing, a rotatable armature within said housing and an axial shaft extending therefrom and having a portion there which is threaded and which is received through a threaded member fixed to said armature; a syringe barrel holder that is fixed relative to the electric motor housing; guide means that is fixed relative to said said syringe barrel holder and including a track extending parallel to said shaft for guiding a portion of said drive; a plunger holder rigidly fixed to said shaft and slidable along said track; said guide means preventing rotational but not axial movement of said shaft upon sliding movement of said plunger holder fixed to said shaft on said track; said track including two elongate members fixed relative to the electric motor housing, said members being parallel spaced from each other and said shaft, and being positioned on either side of said shaft; means for engaging the barrel of a syringe with said syringe barrel holder; and means for connecting the plunger of the syringe to said plunger holder, whereby energization of the electric motor will provide non-rotational axial travel of said shaft thereby moving the syringe plunger axially.

6. A syringe drive as described in claim 5, including means for controlling the electric motor comprising a switch located in the travel path of said plunger holder.

7. A syringe drive as described in claim 5, including means for engaging an additional syringe barrel with said syringe barrel holder, and means for connecting an additional plunger to said plunger holder for operation with said additional barrel.

8. A syringe drive as described in claim 5, said electric motor comprising a reversing motor; means for connecting said electric motor to an electric current source; a plurality of switches in fixed locations relative to said track, said switches being operative to control electrical energization of said electric motor; said plunger holder being operative to actuate and deactuate said switches during axial travel of said shaft.

9. A syringe drive as described in claim 5, wherein said electric motor includes an armature, a nut captured inside the armature and axially positioned, said shaft being threaded and located within and through said nut in threaded engagement therewith, whereby when the threaded shaft is prevented from rotating there will be relative motion between the nut which turns with the armature during energization of the electric motor and the threaded shaft to thereby move the threaded shaft axially.

10. The syringe drive according to claim 1 wherein said first holder is fixed to said elongate members.

11. The syringe drive according to claim 5 wherein said barrel holder is fixed to said elongate members.

* * * * *